United States Patent
Heacock

(10) Patent No.: US 7,281,794 B2
(45) Date of Patent: *Oct. 16, 2007

(54) DISPOSABLE OPHTHALMIC LENS

(75) Inventor: Gregory L. Heacock, 314 NE. Nevada St., Camas, WA (US) 98607

(73) Assignee: Gregory L. Heacock, Auburn, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/995,589

(22) Filed: Nov. 22, 2004

(65) Prior Publication Data

US 2005/0157257 A1    Jul. 21, 2005

Related U.S. Application Data

(63) Continuation of application No. 09/990,934, filed on Nov. 16, 2001, now Pat. No. 6,851,808.

(51) Int. Cl.
*G02C 7/04* (2006.01)

(52) U.S. Cl. .................................. 351/160 R

(58) Field of Classification Search ............... 351/216, 351/218, 219, 246, 247, 159, 160 R, 162, 351/178, 158; 374/45; 134/7; 249/61
See application file for complete search history.

(56) References Cited

U.S. PATENT DOCUMENTS

| | | | | |
|---|---|---|---|---|
| 4,613,379 A | * | 9/1986 | Su et al. ..................... | 134/7 |
| 4,728,183 A | | 3/1988 | Heacock et al. | |
| 4,921,205 A | * | 5/1990 | Drew et al. ................ | 249/61 |
| 5,706,073 A | * | 1/1998 | Volk .......................... | 351/219 |
| 6,471,396 B2 | * | 10/2002 | Biel ........................... | 374/45 |

* cited by examiner

*Primary Examiner*—George Manuel
(74) *Attorney, Agent, or Firm*—McAndrews, Held & Malloy, Ltd.

(57) ABSTRACT

An ophthalmic lens with high definition, wide field of view and high magnification has, in one embodiment, a contact lens, an intermediate field lens and an image lens wherein a real image is formed inside the field lens. At least two of the lenses contribute to the magnification and three surfaces of the ophthalmic lens are aspheric to provide a better defined image. The ophthalmic lens is made disposable with high quality plastic lenses and a plastic holder. A portion of the holder changes appearance in response to change in environment to indicate that the disposable lens has been used.

2 Claims, 1 Drawing Sheet

DISPOSABLE OPHTHALMIC LENS

CROSS-REFERENCE TO RELATED APPLICATIONS

This application is a continuation of U.S. patent application Ser. No. 09/990,934 filed Nov. 16, 2001, now U.S. Pat. No. 6,851,808.

STATEMENT REGARDING FEDERALLY SPONSORED RESEARCH OR DEVELOPMENT

N/A

TECHNICAL FIELD

The present invention relates to an ophthalmic lens for diagnostic and/or surgical uses. The ophthalmic lens provides a wide field of view, high magnification and a well-defined image. The ophthalmic lens is also made to be disposable.

BACKGROUND OF THE INVENTION

Typical ophthalmic lens are such that they have either high magnification and a relatively limited field of view or they have a wide field of view and a low magnification. Depending upon the particular use of the ophthalmic lens, one or the other of these types of ophthalmic lenses is chosen. One known ophthalmic lens as shown in U.S. Pat. No. 4,728,813 includes a contact lens formed of polymethylmethacrylate and an aspheric lens formed of glass. The aspheric lens and contact lens are supported in a housing with a fixed spacing between the lenses. This ophthalmic lens forms a real image of the patient's fundus in air. Another known ophthalmic lens includes three elements, a contact lens and two elements cemented together to form an image lens wherein the lenses are all formed of glass. This ophthalmic lens is such that a real image of the fundus is formed inside the image lens. Moreover, the image lens provides all of the optical power in this ophthalmic lens for magnification of the fundus. As such, the image lens is very thick, being on the order of 1.25 inches. This ophthalmic lens provides a relatively wide field of view but low magnification. Heretofore, a wide field of view and high magnification were thought to be mutually exclusive attributes of an ophthalmic lens.

Because a number of diseases, such as AIDS, can be transmitted by contact with the eye, it is critically important that the ophthalmic lens be sterilized before each use. As such, in all of the known ophthalmic lenses, including. those described above, the housing or holder for the lenses is made of a metal capable of withstanding the high temperatures of autoclaving without degradation. Because of the housing material and the use of glass aspheric lenses, known ophthalmic lenses are extremely costly.

BRIEF SUMMARY OF THE INVENTION

In accordance with the present invention, the disadvantages of prior ophthalmic lenses have been overcome. The ophthalmic lens of the present. invention provides both high magnification and a wide field of view. In accordance with a further feature of the present invention, the ophthalmic lens is made to be disposable.

More particularly, in accordance with one feature of the present invention, a disposable ophthalmic lens includes a plastic holder supporting one or more lenses. A sterile contact lens formed of a transparent plastic is mounted in the holder, the contact lens having a first surface shaped to contact an eye when in use. The holder, with one or more lenses including the contact lens mounted therein, is enclosed in a package that maintains the contact lens free from contamination before use.

In accordance with one embodiment of the present invention, at least a portion of the holder is formed of a material that changes appearance in response to a change in the holder's environment. In a preferred embodiment, the holder portion is formed of a photoreactive material that changes color in the presence of light. In this embodiment, the package is made of a non-light transmissive material so as to prevent the holder portion from changing color while enclosed in the package. After the package is opened and the holder taken out for use, the exposure to light will change the color of the holder portion to indicate that the ophthalmic lens has been used and should be disposed of. Thus, the present invention prevents inadvertent use of an ophthalmic lens that has already been used and is not sterile.

In accordance with a further feature of the present invention, the contact lens is mounted in a first end of the holder, the contact lens having a surface opposite the surface shaped to contact the eye that is aspheric. An intermediate lens is mounted in the holder and spaced between the contact lens and an image lens wherein the intermediate lens bends peripheral rays from the contact lens towards the image lens and contributes optical power to the ophthalmic lens. An image lens is mounted in a second end of the holder with a positive first surface through which rays from the intermediate lens enter and are focused to form a real image inside of the image lens. A second surface of the image lens further magnifies the real image. This ophthalmic lens provides a very wide field of view that is, for example, greater than or equal to 60° and has high magnification. In a preferred embodiment, both the first and second surfaces of the image lens are aspheric surfaces as well as the anterior surface of the contact lens. The three aspheric surfaces contribute to an extremely high quality, well-defined image in addition to the wide field of view and high magnification.

These and other advantages and novel features of the present invention, as well as details of an illustrated embodiment thereof, will be more fully understood from the following description and drawings.

DETAILED DESCRIPTION OF THE INVENTION

Figure 1:
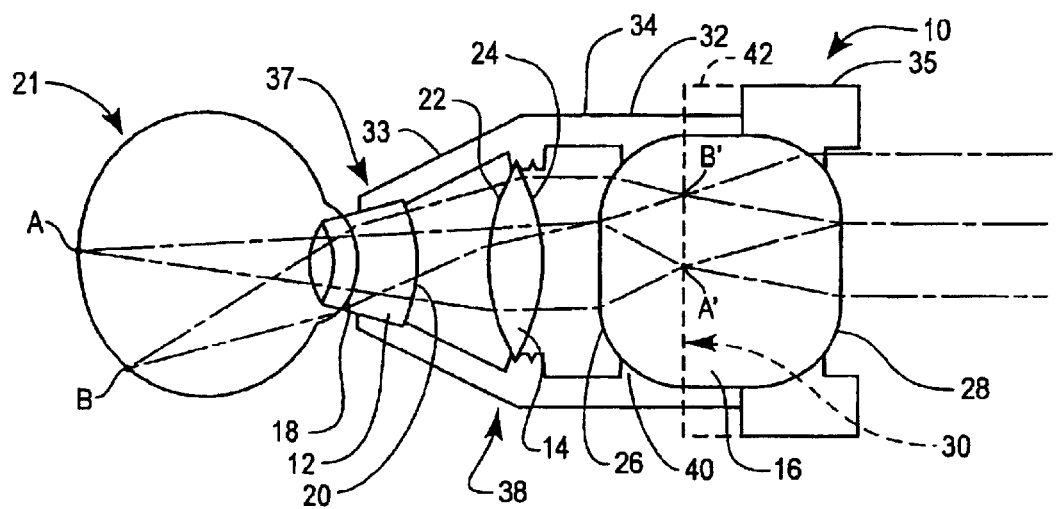
FIG. 1 is a cross-sectional view of an ophthalmic lens in accordance with one embodiment of the present invention having a contact lens, intermediate lens and image lens mounted in a holder for diagnostic and/or surgical use.

The ophthalmic lens 10 of the present invention as shown in FIG. 1 provides a better defined image than known ophthalmic lenses while providing a very wide field of view and high magnification. These advantages are attained by the use of three spaced lenses including a contact lens 12, an intermediate field lens 14 and an image lens 16 wherein a real image of the interior of an eye is formed inside the image lens 16.

More particularly, the contact lens 12 has a surface 18 having an approximate shape of a cornea and is intended to contact the eye in use. For example, the surface 18 may be spherical having a radius of curvature of approximately 7.8 mm, although other radii can be used as will be apparent to one of ordinary skill. The opposite surface 20 of the contact lens 12 is shaped so as to neutralize the optical power of the patient's cornea so that the rays exiting the contact lens from a point on the retina 21 of a patient's eye are approximately parallel.

The rays exiting from the contact lens 12 enter a surface 22 of the field lens 14. The field lens 14 bends the peripheral image rays such as from point B towards the image lens 16. The field lens 14 also contributes to the optical power of the ophthalmic lens 10. Each of the surfaces 22 and 24 of the field lens 14 is a spherical surface. However, one or both of these surfaces can be made aspheric if desired.

Rays enter a positive surface 26 of the image lens 16 and are focused by the positive curvature of the surface 26 to form a real, inverted image of the patient's retina 21 inside of the image lens 16. The opposite or anterior surface 28 of the image lens 16 has a curvature to magnify the real image 30. Further, each of the surfaces 26 and 28 is an aspheric surface.

In a preferred embodiment of the present invention, each of the aspheric surfaces 20, 26 and 28 of the ophthalmic lens is formed of an aspheric surface defined by the following equation.

$$Z = \frac{Cr^2}{1+\sqrt{1-(1+k)C^2r^2}} + A_1 r^2 + A_2 r^4 + A_3 r^6 \ldots .$$

For surface 20, the following values are preferred.

$1/C = 6.82 \pm 1$ $K = -0.27$ $A_1 = -0.00023 \pm 0.1$ $A_2 = 0.000074 \pm 0.1$ $A_3 = 0 \pm 0.001$

For surface 22, the following values are preferred.

$1/C = 24 \pm 3$ $K = -1.65 \pm 0.2$ $A_1 = 0.02 \pm 0.01$ $A_2 = 4 \times 10^{-6} \pm 5 \times 10^{-6}$ $A_3 = 1.3 \times 10^{-8} \pm 1 \times 10^{-8}$ For surface 24, the following values are preferred.

$1/C = -32 \pm 3$ $K = -2.7 \pm 0.5$ $A_1 = 0.003 \pm 0.002$ $A_2 = 4.0 \times 10^{-6} \pm 1.0 \times 10^{-6}$ $A_3 = 9.5 \times 10^{-9} \pm 1.5 \times 10^{-8}$ For surface 26, the following values are preferred.

$1/C = 21.8 \pm 3$ $K = 1.7 \pm 1$ $A_1 = -0.02 \pm 0.01$ $A_2 = 6 \times 10^{-5} \pm 2 \times 10^{-4}$ $A_3 = -4.7 \times 10^{-8} \pm 4.0 \times 10^{-9}$ For surface 28, the following values are preferred.

$1/C = -25$ $K = -3.0 \pm 1$ $A_1 = 0 \pm 0.05$ $A_2 = 0 \pm 0.05$ $A_3 = 0 \pm 0.05$

In accordance with a further feature of the present invention, the ophthalmic lens 10 is made disposable by forming each of the three lenses 12, 14, and 16 of a transparent optical plastic such as polymethylmethacrylate or PMMA. Heretofore, it was thought that lenses having aspheric surfaces should be formed of glass. However, it has been found, that in accordance with the present invention, an aspheric surface such as described above can be formed of an ophthalmic plastic such as PMMA by injection molding, compression molding, casting and further by CNC machining. Moreover, the lenses 12, 14 and 16 are supported in a housing or holder 32 that is also formed of plastic. In particular, the holder 32 is preferably formed of an acrylic, styrene or polycarbonate.

In a preferred embodiment of the present invention, at least a portion of the holder 32 is formed of a material that changes appearance in response to environmental changes. For example, the holder portion can include a dye that changes color in the absence or presence of water. In this embodiment, the ophthalmic lens 10 would be packaged in a sterile saline solution for example. When the lens is taken out of the package, the color of that portion of the holder 32 containing the dye would change color as the ophthalmic lens 10 dries. In a preferred embodiment of the present invention, a portion of the holder 32 includes a dye that changes color as the material absorbs light. A suitable photoreactive or photochromic dye in accordance with this embodiment of the present invention is available from Color Change Corporation of Addison, Illinois. In a preferred embodiment, the color change is also irreversible. The package enclosing an ophthalmic lens 10 with a photoreactive holder portion is preferably formed of a material that is non-light transmissive so that it block light to prevent the lens from changing colors prior to use. When the ophthalmic lens packaging is opened and the ophthalmic lens 10 exposed to light, the holder 32 changes color to indicate that it has been used. The holder 32 may change color, for example, from blue to yellow or green to red such that there is a significant color change to indicate that the ophthalmic lens 10 has already been used and should not be re-used but should be disposed of.

Figure 2:
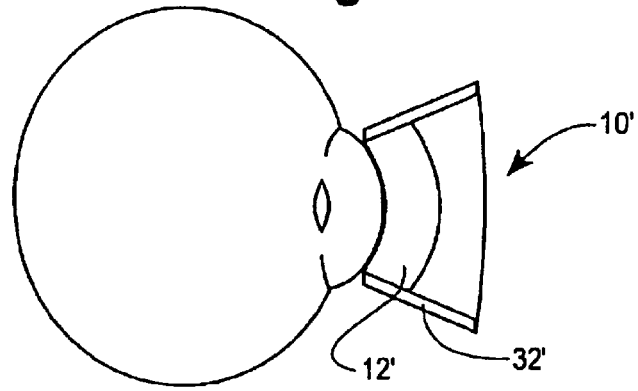
FIG. 2 is a cross-sectional view of an ophthalmic lens in accordance with a second embodiment of the present invention for diagnostic use.

A disposable ophthalmic lens in accordance with the present invention need not have three lenses as illustrated in FIG. 1. In an alternative embodiment as shown in FIG. 2, an ophthalmic lens 10' having a single lens in the form of a fundus contact lens 12' is supported in a cone or holder 32'. In this embodiment, the entire holder 32' is preferably formed of a material containing the photochromic or photoreactive dye. The holder 32, such as shown in FIG. 1, may be formed of multiple sections. For example, a section 33 has an end 37 for supporting the contact lens 12 and an end 38 with a flange for supporting the field lens 14. An intermediate section 34 with another flange may screw onto the section 33 to hold the field lens 14 in place. The section 34 also includes a flange 40 or the like for supporting the image lens 16. A section 35 of the holder 32 preferably screws onto the section 34 of the holder 32 so as to retain the image lens 16 in place. In this embodiment, one or more of the surfaces 33, 34 and 35 can be formed of a material containing the dye that changes appearance in response to environmental changes. In a further embodiment, a member 42 containing the dye that changes appearance in response to environmental changes can be mounted on an outer surface of the holder 32 so as to form a portion of the holder although it is not integral therewith. Other variations of the holder of the present invention can be made as well.

Figure 3:
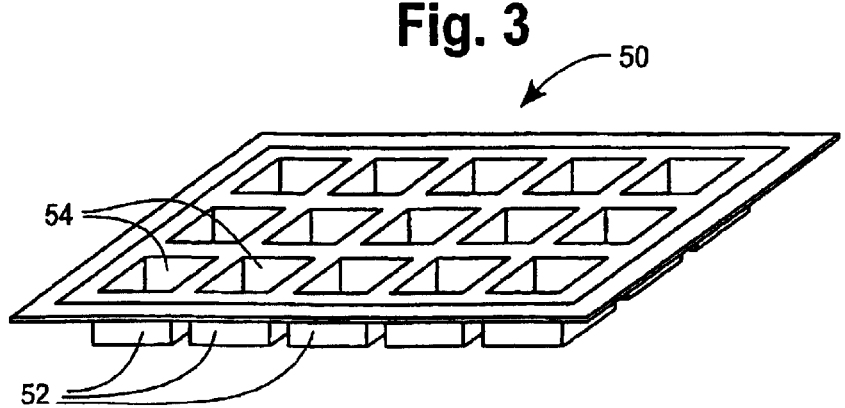
FIG. 3 is a perspective view of one embodiment of a package for a plurality of disposable lenses.

FIG. 3 illustrates one embodiment of a package for a plurality of ophthalmic lenses 10 in accordance with the present invention. In this embodiment, the package is formed of a tray 50 having a number of individual compartments 52 for holding a respective, disposable ophthalmic lens 10. Each compartment 52 has a foil cover 54 or the like that can be individually removed without removing the cover of an adjacent compartment 52 so that one ophthalmic lens 10 can be removed from the tray 50 without altering the environment of the ophthalmic lenses contained in the adjacent compartments 52. In an alternative embodiment, each ophthalmic lens 10 can be contained in its own individual wrapper that controls the environment of the ophthalmic lens 10 prior to use. It should be appreciated that, the ophthalmic lens 10 is sterilized and thereafter packaged wherein the packaging is such that it maintains the ophthalmic lens 10 free from contaminants prior to use.

Many modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. An ophthalmic lens used in contact with an eye comprising:
   a holder supporting a plurality of lenses;
   a contact lens mounted in a first end of the holder, the contact lens having a first surface shaped to contact an eye when in use and a second surface that is aspheric;
   an intermediate lens mounted in the holder and spaced between the contact lens and an image lens, the intermediate lens bending peripheral rays from the contact lens towards the image lens and contributing optical power; and
   an image lens mounted in a second end of the holder with a positive first surface through which rays from the intermediate lens enter and are focused to form a real image inside the lens and a second surface that magnifies the real image wherein the contact lens, intermediate lens and image lens each have a thickness less than 14 mm.

2. An ophthalmic lens used in contact with an eye comprising:
   a holder supporting a plurality of lenses;
   a contact lens mounted in a first end of the holder, the contact lens having a first surface shaped to contact an eye when in use and a second surface that is aspheric;
   an intermediate lens mounted in the holder and spaced between the contact lens and an image lens, the intermediate lens bending peripheral rays from the contact lens towards the image lens and contributing optical power; and
   an image lens mounted in a second end of the holder with a positive first surface through which rays from the intermediate lens enter and are focused to form a real image inside the lens and a second surface that magnifies the real image wherein the contact lens, intermediate lens and image lens each have a thickness less than or approximately equal to 13 mm.

* * * * *